United States Patent [19]

Vilaghy et al.

[11] 4,010,737
[45] Mar. 8, 1977

[54] BONE BIOPSY INSTRUMENT KIT

[76] Inventors: Miklos I. Vilaghy; Gabor Zellerman, both of Apt. 1508, 830 Ontario St., Toronto 282, Canada

[22] Filed: July 18, 1973
[21] Appl. No.: 380,131

Related U.S. Application Data

[63] Continuation of Ser. No. 152,896, June 14, 1971, abandoned.

[52] U.S. Cl. .................. 128/2 B; 30/316; 128/310
[51] Int. Cl.² .......................... A61B 10/00
[58] Field of Search ........... 128/2 R, 2 B, 305, 310, 128/329, 347; 30/316

[56] References Cited

UNITED STATES PATENTS

| | | | |
|---|---|---|---|
| 1,867,624 | 7/1932 | Hoffman | 128/2 B |
| 2,219,605 | 10/1940 | Turkel | 128/2 B |
| 2,266,393 | 12/1941 | Hoffman | 30/316 X |
| 2,426,535 | 8/1947 | Turkel | 128/2 B |
| 2,790,437 | 4/1957 | Moore | 128/2 B |
| 2,850,007 | 9/1958 | Lingley | 128/2 B |
| 2,919,692 | 1/1960 | Ackermann | 128/2 B |
| 3,082,805 | 3/1963 | Royce | 128/2 B X |
| 3,452,741 | 7/1969 | Schaffer | 128/2 B |
| 3,515,128 | 6/1970 | McEvoy | 128/2 B |
| 3,613,662 | 10/1971 | Chrysostomides | 128/2 B |

FOREIGN PATENTS OR APPLICATIONS 373,112  7/1939  Italy ................. 128/2 B

OTHER PUBLICATIONS

Minnesota Medicine, Aug. 1966, pp. 1319-1322.
The Lancet, Mar. 13, 1965, p. 585.

Primary Examiner—Kyle L. Howell
Attorney, Agent, or Firm—Stonebraker, Shepard & Stephens

[57] ABSTRACT

A bone biopsy instrument kit includes a hollow body having a socketed forward end to receive one of several hollow, disposable needles. A chuck holds a needle in place on the body, and the rear end of the body has a recess for receiving a bushing into which a stylet is threaded for extending through the body and the needle as desired. The stylet serves as an obturator closing the needle for passing through soft tissue to the bone, then the body is used to drive the needle into the bone to a depth that can be checked by reinserting the obturator. The removed specimen material is set inside the disposable needle, and then another stylet with a blunt end is used to extrude the specimen from the needle for diagnosis.

12 Claims, 10 Drawing Figures

U.S. Patent  Mar. 8, 1977  4,010,737
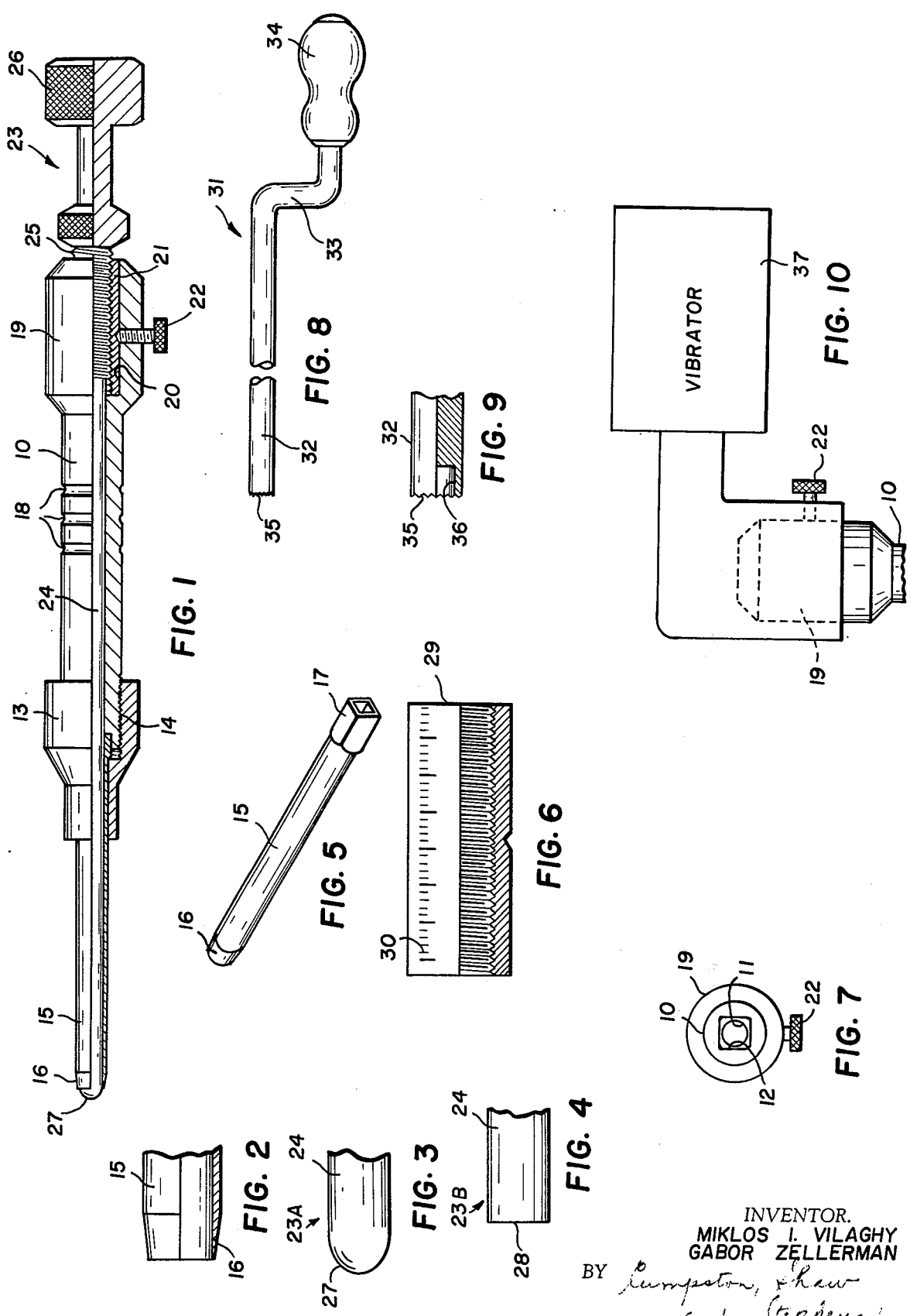

BONE BIOPSY INSTRUMENT KIT

THE INVENTIVE IMPROVEMENT

This is a continuation of application Ser. No. 152,896 filed June 14, 1971, now abandoned.

There are many medical reasons why a bone biopsy specimen is valuable for diagnosis, and it is most desirable to have an unbroken, plug of bone material for this. However, getting such a plug of bone material has been a serious problem. One way is to perform surgery under general or local anesthesia to expose a bone from which a biopsy specimen is cut away. This causes considerable damage to patients, requires a stay in the hospital, and is relatively expensive from use of the operating room.

Some trephines and needles or cannulae have been proposed for biopsies of bone marrow material, but these have not been successful for securing biopsy specimens of the bone itself. They have either produced small or damaged bone specimens or resulted in bone and soft tissue wounds too large for the size of the specimen obtained. One of the more successful of the instruments designed for bone biopsy work is a specially made needle or cannula introduced in 1949. This needle is long and strong with a relatively massive head at one end for gripping, thrusting, or pounding the needle into bone. A stylet or obturator accompanies the needle for use in inserting the needle through soft tissue.

One of the contributions of this invention is recognition of the defects of other bone biopsy methods and equipment and making an improved instrument kit for overcoming such disadvantages. For example, the 1949 needle is relatively expensive and large with a pounding head integral with the needle so that it is not disposable.

However, the head of this needle is not large enough to afford a good grip for pulling the needle out from especially hard bone without assistance from other tools such as pliers or forceps. This needle must be resharpened occasionally, and it gradually becomes shorter and shorter with each sharpening. Also, it is sometimes bent, or broken, and attmepts at straightening it are usually not fully successful. Because of its expense there is not usually a large supply of these needles available so specimens are not generally left in a needle, but are quickly cleared out to make the needle available for additional biopsies. This also damages many specimens. Furthermore, with such a large needle, it would be difficult to set the biopsy specimen while lodged in place in the needle because it would require a relatively large container and a relatively large amount of formaldehyde. Also, as the needle becomes shorter from sharpening, the stylet or obturator must also be shortened so it will not protrude too far beyond the end of the needle. It was sometimes very difficult or impossible to remove a specimen from a needle, at least without serious damage to the specimen. Specimens that were tightly stuck in the needle were driven out by hammering on the rounded end of the stylus that accompanied the needle, and this tended to drive the stylus into the specimen and damage it seriously. All these disadvantages make the prior art bone biopsy equipment difficult and inefficient to use, and the invention not only recognizes this, but proposes a better solution to the problem.

SUMMARY OF THE INVENTION

The inventive improvement uses a plurality of disposable hollow needles held in a hollow instrument body. The forward end of the body has a socket, and each of the needles has a sharp forward end and a rear end shaped to fit into the socket. A hollow chuck screws onto the forward end of the body to hold one of the needles firmly in the socket. A stylet is shaped to move axially through the body and through any one of the needles held in the socket in a free, sliding fit, and there is a screw thread connection between the stylet and the body for selective axial movement of the stylet relative to the body. The screw thread connection is preferably a threaded bushing insertable in a recess at the rear end of the body and removably held in place with a set screw.

The disposable needles eliminate sharpening, bending and breaking problems, allow several biopsies to be taken with the same kit, and allow setting and storing of biopsy specimens in the needles while the basic kit is occupied with other work. The disposable needles also allow different needle sizes of length and wall thickness. The screw thread connection between the stylet and the body allows accurate adjustment of one stylet used as an obturator to fit any length needle, allows accurate measurement of the depth of a needle in a bone by probing with the obturator, and allows another stylet used as an extruder to be screwed into the body for driving the biopsy specimen out of a needle.

DRAWINGS:

FIG. 1 is a partially sectioned, elevational view of a preferred embodiment of an assembled bone biopsy instrument;

FIG. 2 is an enlarged, fragmentary view of a preferred form of needle tip;

FIG. 3 is an enlarged, fragmentary view of a preferred form of obturator tip;

FIG. 4 is an enlarged, fragmentary view of a preferred form of extruder tip;

FIG. 5 is a perspective view of a preferred embodiment of a needle for use in the inventive kit;

FIG. 6 is an enlarged, partially sectioned, elevational view of a preferred, threaded bushing for use in the inventive kit;

FIG. 7 is an end elevation of a preferred embodiment of instrument body;

FIG. 8 is an elevational view of a trephine for use in the inventive kit;

FIG. 9 is an enlarged, partially sectioned, fragmentary view of a preferred tip for the trephine of FIG. 8; and FIG. 10 is a partially schematic, elevational view of a vibrator for use in the inventive kit.

DETAILED DESCRIPTION:

The inventive bone biopsy kit includes several elements that can be assembled in different ways for various medical purposes as described more fully below. All the parts for the kit are preferably arranged in a sterile container for convenient use as is common with medical instruments. However, the container itself and the obvious parts of the kit are not shown, and only the novel and most important parts of preferred embodiments of the kit are shown in the drawings and described below.

The assembled instrument of FIG. 1 includes a body 10 also shown in FIG. 7 as having a hollow bore 11, terminating at the front end of body 10 in a socket 12 that is preferably square and slightly larger than bore 11. A hollow chuck 13 screws onto threads 14 at the forward end of body 10 around socket 12. The kit includes many disposable needles 15 that are also medically known as cannulae. Needles 15 have sharpened forward ends 16 and enlarged and squared rear ends 17 to fit into socket 12. Each of the needles 15 is generally cylindrical with a bore or lumen of the same inside diameter as bore 11 in body 10. One of the needles 15 is inserted through hollow chuck 13 with the square end 17 of the needle fitted in socket 12, and chuck 13 is screwed onto body 10 to hold the needle 15 firmly in body 10. Bore 11 in body 10 aligns with the lumen of needle 15 in a continuous, straight, passageway.

Needles 15 are preferably made of a strong and hard material to withstand pounding and forceful use. Their tips 16 are preferably circular, sharpened as illustrated in FIGS. 1 and 2, and hardened to hold their cutting edge. Since needles 15 are relatively simple and not especially large, they are economical enough to be disposable after use to eliminate re-sharpening. The inventive kit preferably contains needles of different lengths formed of material of different thicknesses for different biopsy work as will be appreciated by those skilled in the art.

Body 10 preferably has grooves 18 or knurling to afford a sure grip for handling the instrument, and body 10 is preferably large enough to allow forceful pulling of the instrument from hard bone. The rear end of body 10 has an enlarged head 19 with a counter bore or recess 20 of larger inside diameter than bore 11 for receiving a threaded bushing 21. A set screw 22 extends through head 19 for securing bushing 21 in place in recess 20.

Preferably a pair of stylets 23 are included in the inventive kit with each stylet 23 having a cylindrical shaft 24 shaped to move axially through bore 11 and needle 15 in a free-sliding fit. Stylets 23 also have screw threads 25 for threading into bushing 21 to form a screw thread connection between stylets 23 and body 10. This allows axial positioning of stylets 23 relative to body 10 and needle 15. Also, enlarged knurled heads 26 on stylets 23 facilitate manual handling of the stylets for purposes described below. Stylets 23 are preferably identical except for the shape of their forward tips which adapt them to different purposes.

FIGS. 3 and 4 show the different forward tips preferred for the shaft 24 of each of the two stylets 23 preferably included with the inventive kit. One stylet is formed with a rounded tip 27 as shown in FIG. 3 to serve as an obturator 23A extending past the cutting edge 16 of needle 15 as shown in FIG. 1 to facilitate the passage of the instrument through soft tissue. Obturator 23A is also used to determine the depth of insertion of needle 15 into the bone as described more fully below. A stylet having blunt tip 28 as shown in FIG. 4 serves as an extruder 23B used for screwing into body 10 to push a bone biopsy specimen out of a needle 15. Knurled head 26 is especially useful on extruder 23B for manually turning extruder 23B into threaded bushing 21 to extrude the specimen out of needle 15.

An alternative bushing 29 shown in FIG. 6 is a substitute for bushing 21. The only difference is in the external marking of a millimeter scale 30 on bushing 29 to indicate the depth of insertion of an obturator 23A into body 10.

The inventive kit preferably includes a trephine 31 as shown in FIGS. 8 and 9. Trephine 31 has a shaft 32 the same diameter as shaft 24 of stylet 23 for a sliding fit in bore 11 and needle 15. Trephine 31 is turned with a crank 22 and a handle 34 for turning sawteeth 35. As best shown in FIG. 9, teeth 35 form a circular saw around a recess 36 in the end of trephine 31.

As schematically shown in FIG. 10, a vibrator 37 is connected to head 19 of body 10 by means of set screw 33. Several vibratory devices are generally known and connectable to body 10 for vibrationally driving the instrument into a bone.

To secure a bone biopsy specimen with the inventive kit, the appropriate needle 15 is selected, inserted through chuck 13 and into socket 12, and secured to body 10 by screwing chuck 13 onto body 10. Then, an obturator 23A having a round tip 27 is screwed into bushing 21 or 29 which is inserted into recess 20 and secured in place by set screw 22 so that tip 27 extends appropriately past the end 16 of needle 15 as illustrated in FIG. 1. After local anesthesia, a small incision is made in the patient in the region where the biopsy is to be secured, and the instrument is pushed through the patient's soft tissue with its open end blocked by obturator 23A, until the tip of needle 15 cuts into the periosteum of the bone to fix the needle in place on the surface of the bone. Then obturator 23A is removed from body 10.

Then body 10 is pushed, vibrated, or hammered to drive needle 15 into the bone to the desired depth. This can be measured by reinserting obturator 23A into body 10 and into contact with the bone material forced up into needle 15. The difference between the original and subsequent depths of insertion of obturator 23A into body 10 indicates the depth of the needle in the bone. Scale 30 on bushing 29 accurately measures this difference. When the desired depth is reached, a twist of body 10 will break off the plug of bone material lodged in needle 15, and body 10 and needle 15 are withdrawn with the bone biopsy material remaining in needle 15. The incision is then closed with a small bandage or tape leaving the patient relatively little discomfort. The local anesthesia, the simplicity and short duration of the operation, and the lack of complications like bleeding and pain, make the inventive method suitable for performance at bedside in hospitals, in private offices, and on an outpatient basis, and this greatly contributes to efficiency and economy.

Chuck 13 is then unscrewed, and needle 15 with its specimen is removed from body 10 and preferably placed in formaldehyde for setting the specimen. If other biopsies are desired, a new needle is fitted to body 10, and the process is repeated. Since many disposable needles 15 are included with each kit, many biopsies can be taken in rapid succession, and many specimens lodged in needles 15 can be setting in formaldehyde or enroute to a laboratory or a pathologist all at one time.

If the specimen does not rest firmly in the needle, or if the intactility of each trabeculas are not very important (for example in specimens taken for hematological reasons) the specimen can be extruded from needle 15 immediately without being set or fixed in formaldehyde.

After the specimen is set, it is pushed out of needle 15 for examination, and a preferred way of doing this is with an extruder 23B having a blunt tip 28 as shown in FIG. 4. A needle 15 having a set specimen is secured to body 10, and then extruder 23B is driven into needle 15 by turning the extruder threads 25 into bushing 21 or 29 to force the specimen from the needle. The powerful and even force thus applied ensures that the specimen is not damaged and that it accurately represents the condition of the bone.

The relatively simple structure of needles 15, limited to the necessary needle shape and socket, allows needles 15 to be discarded after each use, or at least when they become bent or dull. This eliminates many previous problems of bending, breaking and sharpening of the bone biopsy needles. Also, the many needles in a single kit allow much more versatility and efficiency in using the kit.

For bones having an especially hard outer surface, trephine 31 is used to saw a circular kerf from the surface of the bone before driving needle 15 into the bone. For such use, the instrument is assembled as previously described, and moved into contact with the bone to be biopsied. Then obturator 23A is withdrawn, and trephine 31 is inserted through body 10 and needle 15 into contact with the bone. Trephine 31 is turned by crank 33 and handle 34 for sawing into the bone surface, then trephine 31 is withdrawn. Body 10 is then thrust, hammered or vibrated to drive needle 15 through the kerf and into the bone to secure a biopsy specimen as previously described.

Persons wishing to practice the invention should remember that other embodiments and variations can be adapted to particular circumstances. Even though one point of view is necessarily chosen in describing and defining the invention, this should not inhibit broader or related embodiments going beyond the semantic orientation of the application but falling within the spirit of the invention. For example, those skilled in the art will appreciate the efficiency and economy of the inventive kit with its disposable needles and improved operating ability. They will understand the many medical uses of the kit, and will know how to apply it in an optimum way under various circumstances.

We claim:

1. A bone biopsy instrument kit having a plurality of parts shaped for selective interconnection to form a bone biopsy tool, said kit comprising:
   a. a body having an axial bore and shaped to serve as a handle;
   b. a forward region of said body having a socket radially larger than said axial bore and formed around said axial bore;
   c. a selected one of a plurality of interchangeable needles being seated in said socket, and each of said needles being generally cylindrical, hollow and strong enough to be driven axially into a bone, the hollow interior of said selected one of said needles being aligned with said axial bore of said body;
   d. each of said needles having a rear region with a substantially identical radial enlargement shaped to fit removably into said socket around said axial bore of said body;
   e. a forward end of each of said needles terminating in a plane perpendicular to the cylindrical axis of each of said needles;
   f. an external bevel sharpening said forward end of each of said needles to a circular knife edge suitable for driving straight into bone;
   g. a hollow chuck having a bore snugly receiving the cylindrical portion of said selected one of said needles to engage said radial enlargement in said rear region of said selected one of said needles;
   h. means fastening said chuck to said forward region of said body so said chuck holds said rear region of said selected one of said needles firmly in said socket;
   i. a stylet having a shaft extending through said body and shaped for moving axially in a snug, sliding fit through said bore of said body and through said selected one of said needles held in said socket by said chuck; and
   j. screw thread means connecting said stylet to said body for moving and positioning a forward end of said stylet axially relative to said forward end of said selected one of said needles as a function of the threading together of the parts of said screw thread connecting means, said body, said selected one of said needles, said chuck, said stylet, and said screw thread connecting means forming said bone biopsy tool when assembled as defined.

2. The kit of claim 1 wherein said screw thread connecting means includes a threaded region on said stylet shaft, a bushing having threads mating with said threaded region of said stylet shaft, and a rear region of said body having a recess removably receiving said bushing in said body.

3. The kit of claim 2 including a set screw releasably holding said bushing in said recess.

4. The kit of claim 3 including a plurality of interchangeable ones of said stylets each having said threaded region mating with said bushing threads for said connection to said body, and wherein said forward end of one of said stylets is rounded and said forward end of another one of said stylets is blunt.

5. The kit of claim 2 wherein the exterior of said bushing has a measuring scale.

6. The kit of claim 1 wherein said needles are of different lengths.

7. The kit of claim 1 wherein said radial enlargement of said needles has the same shape as said socket around said axial bore of said body.

8. The kit of claim 1 including a plurality of interchangeable ones of said stylets each shaped to mate with said screw thread connecting means for said connection to said body, and wherein said forward end of one of said stylets is rounded and said forward end of another one of said stylets is blunt.

9. The kit of claim 1 wherein a rear region of said body has an enlarged head configured for gripping and pounding, said enlarged head has a recess, said screw thread connecting means includes a threaded bushing removably held in said recess, and a threaded region of said stylet shaft mates with said bushing.

10. The kit of claim 9 including a plurality of interchangeable ones of said stylets each having said threaded region mating with said bushing for said connection to said body, and wherein said forward end of one of said stylets is rounded and said forward end of another one of said stylets is blunt.

11. The kit of claim 10 including a set screw releasably holding said bushing in said recess.

12. The kit of claim 11 wherein said socket around said axial bore is polygonal, said needles are of different lengths, and said rear regions of said needles are made correspondingly polygonal to form said radial enlargement and to fit said socket.

* * * * *